US012788931B2

(12) United States Patent
Chen et al.

(10) Patent No.: US 12,788,931 B2
(45) Date of Patent: Nov. 10, 2026

(54) FLUID PASSAGE/STOP BODY, COMPONENT, HOUSING AND APPARATUS, VENTILATION TREATMENT DEVICE, AND OXYGEN SUPPLY CONTROL METHOD

(71) Applicant: BMC MEDICAL CO., LTD., Beijing (CN)

(72) Inventors: Yunjing Chen, Tianjin (CN); Jiuzhong Liu, Tianjin (CN); Zhi Zhuang, Beijing (CN); Fang Zheng, Tianjin (CN); Anjun Zhang, Beijing (CN)

(73) Assignee: BMC MEDICAL CO., LTD., Beijing (CN)

( * ) Notice: Subject to any disclaimer, the term of this patent is extended or adjusted under 35 U.S.C. 154(b) by 719 days.

(21) Appl. No.: 18/269,111

(22) PCT Filed: Nov. 12, 2021

(86) PCT No.: PCT/CN2021/130309
§ 371 (c)(1),
(2) Date: Jun. 22, 2023

(87) PCT Pub. No.: WO2022/142769
PCT Pub. Date: Jul. 7, 2022

(65) Prior Publication Data

US 2024/0299687 A1 Sep. 12, 2024

(30) Foreign Application Priority Data

Dec. 30, 2020 (CN) ......................... 202011607982.2

(51) Int. Cl.
*A61M 16/12* (2006.01)
*A61M 16/00* (2006.01)
(Continued)

(52) U.S. Cl.
CPC ........ *A61M 16/12* (2013.01); *A61M 16/0066* (2013.01); *A61M 16/1075* (2013.01);
(Continued)

(58) Field of Classification Search
CPC .............. A61M 16/12; A61M 16/0066; A61M 16/1075; A61M 16/125; A61M 16/206;
(Continued)

(56) References Cited

U.S. PATENT DOCUMENTS 3,727,627 A * 4/1973 Bird ...................... A61M 16/20
137/100
5,501,213 A 3/1996 Jackson
(Continued)

FOREIGN PATENT DOCUMENTS

CN 102182833 A 9/2011
CN 102470226 A 5/2012
(Continued)

OTHER PUBLICATIONS

DE 4343205 A1 (Year: 1995).*
(Continued)

*Primary Examiner* — Victoria Murphy
(74) *Attorney, Agent, or Firm* — Volpe Koenig

(57) ABSTRACT

A fluid passage/stop body, component, housing and apparatus, a ventilation treatment device, and an oxygen supply control method. The fluid passage/stop body comprises a sliding plate and a flexible connecting member; the flexible connecting member is connected to the sliding plate; the flexible connecting member is used for connecting to a first channel wall of a first fluid channel of a fluid passage/stop apparatus; and the sliding plate is used for moving, driven by the pressure of a fluid in the first fluid channel, to drive the flexible connecting member to flexibly deform. The fluid passage/stop body is simple in structure, can drive, in actual
(Continued)

use, a passage/stop member to safely and reliably achieve the passage/stop of a fluid, and can significantly improve, in a ventilation treatment device, the safety of oxygen supply of the ventilation treatment device.

16 Claims, 7 Drawing Sheets

(51) Int. Cl.
*A61M 16/10* (2006.01)
*A61M 16/20* (2006.01)

(52) U.S. Cl.
CPC ........ *A61M 16/125* (2014.02); *A61M 16/206* (2014.02); *A61M 16/208* (2013.01); *A61M 2202/0208* (2013.01)

(58) Field of Classification Search
CPC ........ A61M 16/208; A61M 2202/0208; A61M 16/0677; A61M 16/00; A61M 16/0003; A61M 2016/0027; F16K 7/07
See application file for complete search history.

(56) References Cited

U.S. PATENT DOCUMENTS

| | | | | |
|---|---|---|---|---|
| 5,666,945 | A | 9/1997 | Davenport | |
| 6,269,813 | B1 | 8/2001 | Fitzgerald et al. | |
| 9,119,976 | B2 | 9/2015 | Rittner et al. | |
| 2004/0144385 | A1* | 7/2004 | Bromster ............ | A61M 16/207 128/205.13 |
| 2012/0138052 | A1 | 6/2012 | Hearn et al. | |
| 2016/0038702 | A1 | 2/2016 | Tanoue et al. | |
| 2018/0243527 | A1* | 8/2018 | Zapol ...................... | C01B 21/32 |

FOREIGN PATENT DOCUMENTS

| | | | |
|---|---|---|---|
| CN | 104105524 | A | 10/2014 |
| CN | 109771772 | A | 5/2019 |
| CN | 209229044 | U | 8/2019 |
| CN | 209444948 | U | 9/2019 |
| CN | 110878858 | A | 3/2020 |
| CN | 111734864 | A | 10/2020 |
| CN | 112691269 | A | 4/2021 |
| CN | 215386666 | U | 1/2022 |
| DE | 4343205 | A1 | 6/1995 |
| WO | 2013074763 | A1 | 5/2013 |
| WO | 2017222913 | A1 | 12/2017 |

OTHER PUBLICATIONS

Chinese Office Action issued on Jun. 18, 2025 for Chinese Patent Application No. 202011607982.2.

Extended European Search Report issued on Mar. 18, 2024 for European Patent Application No. 21913512.6.

* cited by examiner

FLUID PASSAGE/STOP BODY, COMPONENT, HOUSING AND APPARATUS, VENTILATION TREATMENT DEVICE, AND OXYGEN SUPPLY CONTROL METHOD

CROSS REFERENCE TO RELATED APPLICATIONS

This application is a 35 USC § 371 National Stage application of International Patent Application No. PCT/CN2021/130309, which was filed Nov. 12, 2021, entitled "FLUID PASSAGE/STOP BODY, COMPONENT, HOUSING AND APPARATUS, VENTILATION TREATMENT DEVICE, AND OXYGEN SUPPLY CONTROL METHOD" and claims priority to Chinese Patent Application No. 202011607982.2 filed on Dec. 30, 2020, which are incorporated herein by reference as if fully set forth.

TECHNICAL FIELD

The present disclosure relates to the field of fluid on/off, in particular to a fluid on/off body, a fluid on/off component, a fluid on/off housing, a fluid on/off apparatus, an oxygen supply control method, and a ventilation treatment device.

BACKGROUND

At present, ventilation treatment devices are vital medical devices for patients with respiratory failure to maintain breathing, ensure ventilation, and save and prolong their lives. ventilation treatment methods based on ventilation treatment devices are an effective way to replace the artificial autonomous ventilation function, and have widely applied in respiratory failure resulted from various reasons, anesthesia and respiratory control during major surgeries, respiratory support therapy, and first-aid and resuscitation.

In a ventilation treatment device, an oxygen source is connected to a flow meter arranged outside the ventilation treatment device, the start and stop of oxygen supply in the entire machine can be controlled and the flow rate of the oxygen can be set by turning a knob on the flow meter.

In actual use, if the operator forgets to shut off the oxygen supply after the machine is used or the machine is shut down owing failures during use but the flow meter is not shut off, the external oxygen will be supplied into the machine persistently, resulting in oxygen waste and other accidents. In case of fire in the machine, the risk of leaving the oxygen in a supplied state will be higher.

SUMMARY OF THE INVENTION

In a first aspect, the present disclosure provides a fluid on/off body, which is simple in structure, can drive, in actual use, an on/off member to safely and reliably block or unblock a fluid channel. For example, when the fluid on/off body is applied in a ventilation treatment device, it can significantly improve the safety of oxygen supply of the ventilation treatment device.

To attain the above object, the present disclosure provides a fluid on/off body, which comprises a sliding plate and a flexible connecting member, wherein the flexible connecting member is connected to the sliding plate, and is configured to connect to a first channel wall of a first fluid channel of a fluid on/off apparatus, the sliding plate is configured to move, driven by the pressure of a fluid in the first fluid channel, to drive the flexible connecting member to deform flexibly.

In the technical scheme, the flexible connecting member is configured to connect to a first channel wall of a first fluid channel of the fluid on/off apparatus, and the sliding plate is configured to move under the pressure of the fluid in the first fluid channel to drive the flexible connecting member to deform flexibly; thus, in actual use of the fluid on/off body, the flexible connecting member can be connected to the first channel wall of the first fluid channel of the fluid on/off apparatus, the on/off member can be connected to the sliding plate, the on/off member can extend from the first fluid channel of the fluid on/off apparatus into a second fluid channel isolated from the first fluid channel in the fluid on/off apparatus and is movable; thus, when the first fluid is not supplied through the first fluid channel, the on/off member can block the second fluid channel to stop the supply of a second fluid; when the first fluid is supplied through the first fluid channel, the first fluid applies pressure on the sliding plate, the flexible connecting member is deformed flexibly, the pressure applied by the first fluid on the sliding plate drives the sliding plate to move, thereby drive the on/off member to move to unblock the second fluid channel, so that the second fluid channel can supply the second fluid. In that way, the supply of the second fluid can be controlled by controlling the supply of the first fluid, thereby the safety and reliability of the supply of the second fluid can be improved. For example, when the fluid on/off body is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

In a second aspect, the present disclosure provides a fluid on/off component, which comprises an on/off member and the fluid on/off body as described above in the first aspect, wherein the on/off member is connected to the sliding plate; wherein the on/off member is configured to extend from the first fluid channel of the fluid on/off apparatus into a second fluid channel isolated from the first fluid channel and is movable; and wherein the on/off member is configured to block the second fluid channel, the sliding plate is configured to move under the pressure of the fluid in the first fluid channel to drive the on/off member to act to unblock the second fluid channel.

Thus, as described above in the first aspect, during actual use, the flexible connecting member may be connected to the first channel wall of the first fluid channel of a fluid on/off apparatus, the on/off member may extend from the first fluid channel of the fluid on/off apparatus into a second fluid channel isolated from the first fluid channel in the fluid on/off apparatus and is movable; thus, when the first fluid is not supplied through the first fluid channel, the on/off member can block the second fluid channel to stop the supply of the second fluid; when the first fluid is supplied through the first fluid channel, the first fluid applies pressure on the sliding plate, the flexible connecting member is deformed flexibly, the pressure applied by the first fluid on the sliding plate drives the sliding plate to move, thereby drive the on/off member to move so as to unblock the second fluid channel, thereby the second fluid can be supplied through the second fluid channel. In that way, the supply of the second fluid can be controlled by controlling the supply of the first fluid, thereby the safety and reliability of the supply of the second fluid can be improved. For example, when the fluid on/off component is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

In a third aspect, the present disclosure provides a fluid on/off housing, in which a first fluid channel and a second fluid channel that are isolated from each other are provided, wherein a first channel wall of the first fluid channel is configured to connect the flexible connecting member of the fluid on/off component as described above in the second aspect; the first channel wall has an opening, the rim of which is configured to connect the flexible connecting member of the fluid on/off component as described above in the second aspect, so that the fluid on/off body of the fluid on/off component as described above in the second aspect serves as a part of the first channel wall.

Thus, in actual use, the fluid on/off housing can connect the flexible connecting member of the fluid on/off component as described above in the second aspect to the rim of the opening. In that way, the fluid on/off body serves as a part of the first channel wall, the on/off member can extend from the first fluid channel of the fluid on/off apparatus into a second fluid channel isolated from the first fluid channel in the fluid on/off apparatus and is movable; thus, when the first fluid is not supplied through the first fluid channel, the on/off member can block the second fluid channel to stop the supply of the second fluid; when the first fluid is supplied through the first fluid channel, the first fluid applies pressure on the sliding plate, the flexible connecting member is deformed flexibly, the pressure applied by the first fluid on the sliding plate drives the sliding plate to move, thereby drive the on/off member to move so as to unblock the second fluid channel, thereby the second fluid can be supplied through the second fluid channel. In that way, the supply of the second fluid can be controlled by controlling the supply of the first fluid, thereby the safety and reliability of the supply of the second fluid can be improved. For example, when the fluid on/off housing is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

In a fourth aspect, the present disclosure provides a fluid on/off apparatus, which comprises: a fluid on/off housing, in which a first fluid channel and a second fluid channel that are isolated from each other are provided; a fluid on/off component, comprising a fluid on/off body and an on/off member, wherein the fluid on/off body is movably arranged in the first fluid channel, the on/off member is connected to the fluid on/off body, and the on/off member extends into the second fluid channel from the first fluid channel and is movable; wherein the on/off member blocks the second fluid channel when the pressure applied by a first fluid in the first fluid channel on the fluid on/off body is smaller than a pressure required for the fluid on/off body to move; and wherein the fluid on/off body moves and drives the on/off member to move to unblock the second fluid channel when the pressure applied by the first fluid in the first fluid channel on the fluid on/off body is greater than the pressure required for the fluid on/off body to move.

In the technical scheme, the fluid on/off body is arranged in the first fluid channel in a movable manner, the on/off member is connected to the fluid on/off body, the on/off member extends from the first fluid channel into the second fluid channel and is movable; when the pressure in the first fluid channel applied on the fluid on/off body is smaller than a pressure required for the fluid on/off body to move, for example, when the supply of the first fluid in the first fluid channel is stopped, the on/off member blocks the second fluid channel so as to stop the supply of the second fluid through the second fluid channel; when the first fluid is supplied through the first fluid channel and the pressure of the first fluid in the first fluid channel applied on the fluid on/off body is greater than the pressure required for the fluid on/off body to move, the fluid on/off body can move and drive the on/off member to move, so as to unblock the second fluid channel to supply the second fluid. In that way, the supply of the second fluid can be controlled by controlling the supply of the first fluid, thereby the safety and reliability of the supply of the second fluid can be improved. For example, when the fluid on/off apparatus is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

In a fifth aspect, the present disclosure provides an oxygen supply control method for controlling the oxygen supply of a ventilation treatment device, which comprises: arranging an oxygen valve in an oxygen supply channel and an air supply channel that is in communication with a fan; controlling the air flow provided by a fan to apply pressure on an oxygen valve so that the oxygen valve opens the oxygen supply channel to supply oxygen, when the ventilation treatment device is powered on and the fan operates; and controlling the oxygen valve to block the oxygen supply channel to stop the oxygen supply when the ventilation treatment device is powered off or the fan is abnormal or the fan stops owing to circuit abnormalities during the operation of the ventilation treatment device.

Thus, the supply of oxygen cay be controlled stably and reliably by means of an oxygen valve arranged movably in an oxygen supply channel and an air supply channel in communication with the fan and by utilizing the pressure applied by the air flow supplied by the fan, thereby oxygen waste can be avoided, and the safety of use of oxygen in the ventilation treatment device can be improved significantly.

In a sixth aspect, the present disclosure provides a ventilation treatment device, which comprises a fan and the fluid on/off apparatus as described above in the fourth aspect, wherein the first fluid channel serves as an air delivery channel, an inlet end of the first fluid channel is in communication with an outlet end of the fan, and the second fluid channel serves as an oxygen delivery channel. Thus, as described above, the safety of use of oxygen in the ventilation treatment device can be improved significantly. Alternatively, the ventilation treatment device can implement the oxygen supply control method as described above in the fifth aspect. Thus, as described above, the safety of use of oxygen in the ventilation treatment device can be improved significantly.

Other features and advantages of the present disclosure will be further detailed in the following embodiments.

BRIEF DESCRIPTION OF THE DRAWINGS

The accompanying drawings are provided herein to facilitate further understanding on the present disclosure and constitute a part of this document. They are used in conjunction with the following embodiments to explain the present disclosure, but are not intended to constitute any limitation to the present disclosure. In the figures.

DESCRIPTION OF EMBODIMENTS

Figure 1:
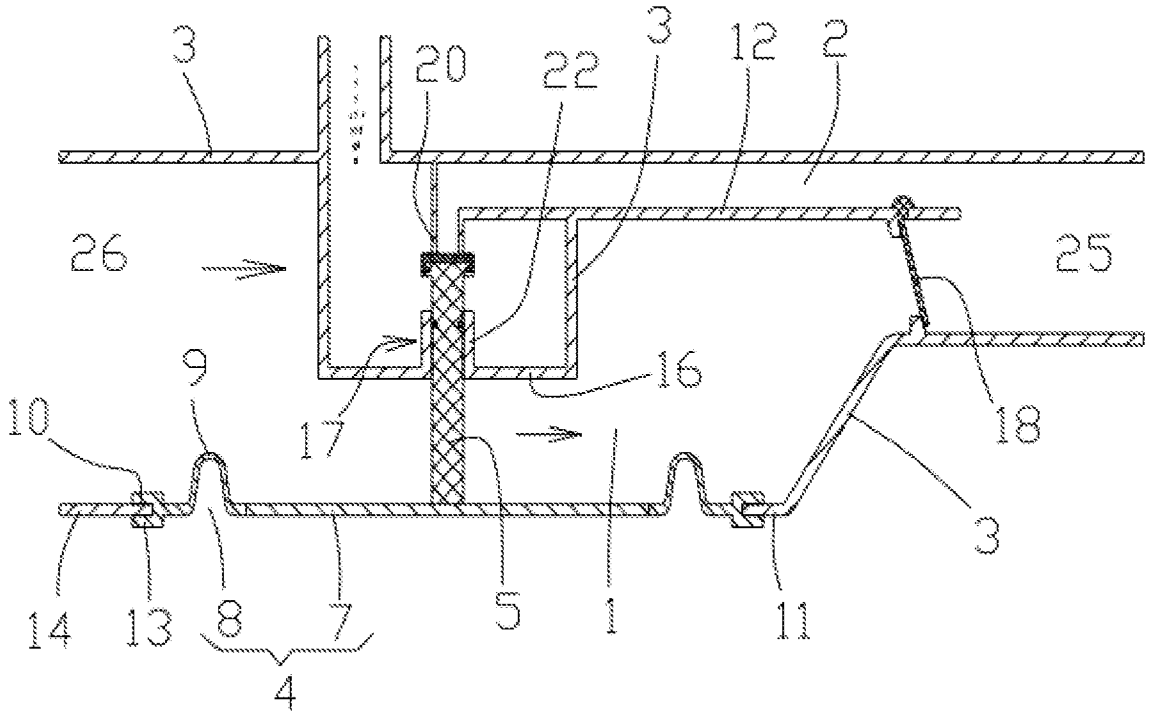
FIG. 1 is a schematic structural diagram of a fluid on/off apparatus provided in first embodiment of the present disclosure, in which the on/off member blocks the second fluid channel.

Some embodiments of the present disclosure will be detailed below with reference to the accompanying drawings. It should be understood that the embodiments described herein are only provided to describe and explain the present disclosure, but are not intended to constitute any limitation to the present disclosure.

Please see the six different embodiments shown in FIGS. 1-12. In a first aspect, the fluid on/off body 4 (e.g., a pressed movable component) provided by the present disclosure comprises a sliding plate 7 and a flexible connecting member, wherein the flexible connecting member is connected to the sliding plate 7, and is configured to connect to a first channel wall 11 of a first fluid channel 1 of a fluid on/off apparatus, and the sliding plate 7 is configured to move under the pressure of a fluid in the first fluid channel 1 to drive the flexible connecting member to flexibly deform.

The flexible connecting member is configured to connect to a first channel wall 11 of a first fluid channel 1 of a fluid on/off apparatus, and the sliding plate 7 can move under the pressure of the fluid in the first fluid channel 1 to drive the flexible connecting member to deform flexibly; thus, during actual use of the fluid on/off body 4, the flexible connecting member may be connected to the first channel wall 11 of the first fluid channel 1 of the fluid on/off apparatus, an on/off member 5 may be connected to the sliding plate 7, the on/off member 5 may extend from the first fluid channel 1 of the fluid on/off apparatus into a second fluid channel 2 isolated from the first fluid channel 1 in the fluid on/off apparatus and is movable. In that way, when the first fluid is not supplied through the first fluid channel 1, the on/off member 5 can block the second fluid channel 2 to stop the supply of the second fluid; when the first fluid is supplied through the first fluid channel 1, the first fluid applies pressure on the sliding plate 7, the flexible connecting member is deformed flexibly, the pressure applied by the first fluid on the sliding plate 7 drives the sliding plate 7 to move, thereby drive the on/off member 5 to move so as to unblock the second fluid channel, thereby the second fluid can be supplied through the second fluid channel. In that way, the supply of the second fluid can be controlled by controlling the supply of the first fluid, thereby the safety and reliability of the supply of the second fluid can be improved. For example, when the fluid on/off body is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

The flexible connecting member may be in a variety of structural forms; for example, the flexible connecting member may be a flexible strip, one end of the flexible strip in the length direction of the flexible strip may be connected to the sliding plate 7, and the other end of the flexible strip in the length direction of the flexible strip may be configured to connect to the first channel wall 11. Alternatively, the flexible strip may be arranged in the circumferential direction of the sliding plate 7, which is to say, the flexible strip extends in the circumferential direction and is connected to the edges of the sliding plate 7.

Or, in an alternative embodiment, the flexible connecting member is an annular flexible connecting member and connected to the periphery of the sliding plate 7; thus, the flexible connecting member can be entirely deformed flexibly in the circumferential direction of the sliding plate 7, so that the movement of the sliding plate 7 is more balanced, more smoothly and more stably.

Moreover, the annular flexible connecting member may be connected to the periphery of the sliding plate 7 to form a flexible skirt; thus, the flexible connecting member can be formed easily, and can be connected to the first channel wall 11 easily.

Moreover, in the fluid on/off body 4, the flexible connecting member may have no elasticity; thus, after the supply of the first fluid is stopped, the sliding plate 7 can be returned to its original position manually, or by means of an elastic member connected to the sliding plate 7, or by means of an elastic member connected to the on/off member 5.

Figure 2:
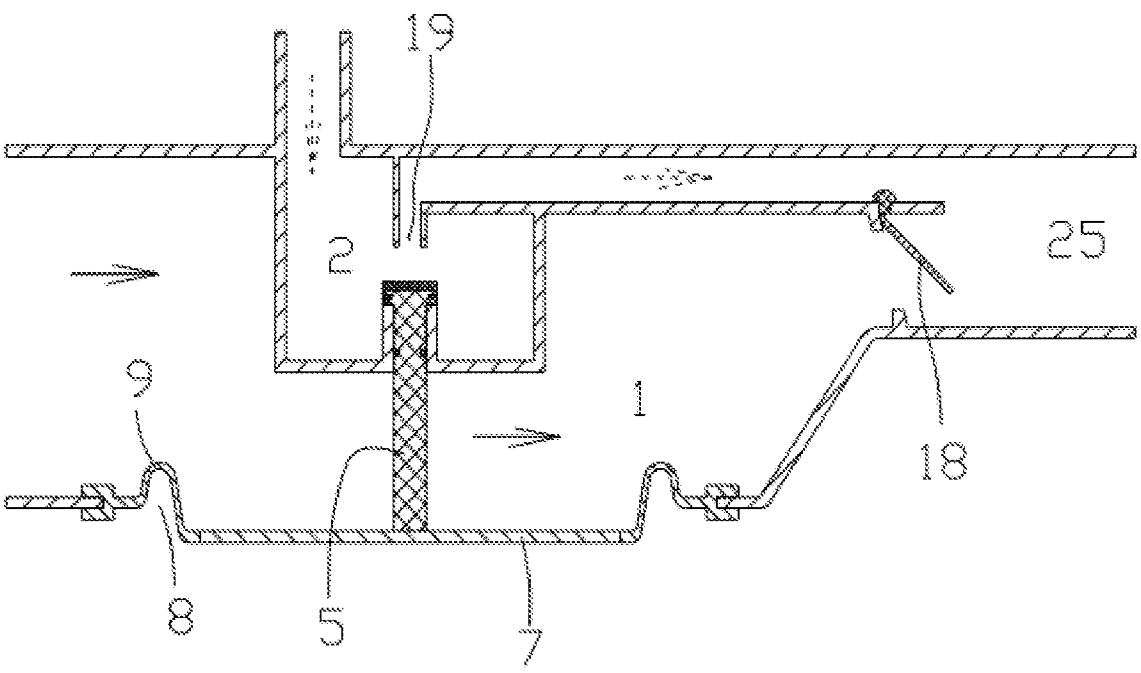
FIG. 2 is a schematic diagram of the fluid on/off apparatus in FIG. 1, in which the on/off member unblocks the second fluid channel.

Moreover, in an alternative embodiment, as shown in FIGS. 1 and 2, the flexible connecting member is an elastic skirt 8. Thus, the elastic skirt 8 can return to its original position under the action its elastic force; in addition, after the elastic skirt 8 returns to its original position, the elastic skirt 8 may be used to apply a pre-pressure on the on/off member 5 connected to the sliding plate 7, so that the on/off member 5 keeps the second fluid channel 2 in a blocked state under the pre-pressure. Here, when the first fluid is supplied, the pressure of the first fluid applied on the sliding plate 7 has to overcome the pre-pressure applied by the elastic skirt 8 before the elastic skirt 8 can be deformed elastically to allow the sliding plate 7 to move, so as to drive the on/off member 5 to move to unblock the second fluid channel 2.

Moreover, in actual use, either side of the sliding plate 7 may be used as the surface on which the pressure of the first fluid is applied, depending on the specific structure of the fluid on/off body.

In addition, in actual use, a variety of different structures may be provided on the first channel wall 11 to connect the flexible connecting member. For example, in an embodiment, the first channel wall 11 has a cylinder extending inward, a fluid inlet is formed in the cylindrical wall of the cylinder, and the flexible connecting member may be connected to a radial inner opening of the cylinder; thus, the first fluid may enter the cylinder via the fluid inlet to apply pressure on the side of the sliding plate 7 facing the interior of the cylinder. Alternatively, in another embodiment, the flexible connecting member is configured to connect to the rim 14 of an opening formed on the first channel wall 11, so that the fluid on/off body 4 serves as a part of the first channel wall 11. That is to say, an opening is formed on the first channel wall 11, the flexible connecting member may be connected to the rim 14 of the opening, so that the sliding plate 7 is located inside the opening; thus, the fluid on/off body 4 forms a part of the first channel wall 11. In that way, when the first fluid flows in the first fluid channel, it can apply pressure on the side of the sliding plate 7 that faces the interior of the first fluid channel 1, and the pressure can drive the sliding plate 7 to move outward; after the pressure is canceled, for example, when the pressure is recovered to the normal atmosphere, the sliding plate 7 moves inward to its original position.

In addition, as shown in FIGS. 1 and 2, to enable the sliding plate 7 to have a greater stroke of movement, the flexible connecting member comprises a U-shaped wall 9 for extending into the first fluid channel 1; thus, the U-shaped wall 9 can utilize its bent side walls to effectively increase the stroke of the sliding plate 7. For example, in the case that the flexible connecting member is an elastic skirt 8, the U-shaped wall 9 can store higher elastic return energy, so that the sliding plate 7 can be returned to its original position more easily, and a higher pre-pressure can be applied on the on/off member 5 connected to the sliding plate 7, so that the on/off member 5 can block the second fluid channel 2 more stably and more reliably.

In addition, in actual use, the flexible connecting member may be connected to the first channel wall 11 in a variety of ways. For example, the flexible connecting member may be connected to the first channel wall 11 by bolting, fusion bonding, or snap-fitting. For example, as shown in FIG. 1, the periphery of the flexible connecting member is connected with a connecting body 13, which has a radial snap groove 10 formed on the outer peripheral surface thereof. Thus, the snap groove 10 may be snapped to corresponding snap edges of the first channel wall 11 conveniently and quickly; for example, as shown in FIG. 1, the snap groove 10 may be snapped to the rim 14 of the opening.

In a second aspect, the present disclosure provides a fluid on/off component, which comprises an on/off member 5 and the fluid on/off body 4 as described above in the first aspect, wherein the on/off member 5 is connected to the sliding plate 7; wherein the on/off member 5 is configured to extend from the first fluid channel 1 of the fluid on/off apparatus into a second fluid channel 2 isolated from the first fluid channel 1 in the fluid on/off apparatus and is movable; and wherein the on/off member 5 is configured to block the second fluid channel 2, and the sliding plate 7 can move under the pressure of the fluid in the first fluid channel 1 to drive the on/off member 5 to move, so as to unblock the second fluid channel 2.

Thus, as described above in the first aspect, during actual use, the flexible connecting member may be connected to the first channel wall 11 of the first fluid channel 1 of a fluid on/off apparatus, the on/off member 5 may extend from the first fluid channel 1 of the fluid on/off apparatus into a second fluid channel 2 in the fluid on/off apparatus; thus, when the first fluid is not supplied through the first fluid channel 1, the on/off member 5 can block the second fluid channel 2 to stop the supply of the second fluid; when the first fluid is supplied through the first fluid channel 1, the first fluid applies pressure on the sliding plate 7, the flexible connecting member is deformed flexibly, the pressure applied by the first fluid on the sliding plate 7 drives the sliding plate 7 to move, thereby drive the on/off member 5 to move so as to unblock the second fluid channel, thereby the second fluid can be supplied through the second fluid channel. In that way, the supply of the second fluid can be controlled by controlling the supply of the first fluid, thereby the safety and reliability of the supply of the second fluid can be improved. For example, when the fluid on/off component is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

In addition, the on/off member 5 may be a plate member or columnar member.

In addition, as shown in FIG. 1, the on/off member 5 is connected to the center of the sliding plate 7; thus, the sliding plate 7 can drive the on/off member 5 to move more stably as the sliding plate 7 moves.

In addition, the on/off member 5 may be detachably connected to the sliding plate 7; thus, during actual use, the on/off member 5 or the sliding plate 7 may be replaced conveniently and quickly according to the damage condition. Of course, alternatively the on/off member 5 and the sliding plate 7 may be formed integrally.

In a third aspect, the present disclosure provides a fluid on/off housing. As shown in FIGS. 1 and 2, in the fluid on/off housing 3, a first fluid channel 1 and a second fluid channel 2 that are isolated from each other are provided, wherein a first channel wall 11 of the first fluid channel 1 is configured to connect the flexible connecting member of the fluid on/off component as described above in the second aspect; the first channel wall 11 has an opening, the rim 14 of which is configured to connect the flexible connecting member of the fluid on/off component as described above in the second aspect, so that the fluid on/off body 4 of the fluid on/off component as described above in the second aspect serves as a part of the first channel wall 11.

Thus, in actual use, the fluid on/off housing can connect the flexible connecting member of the fluid on/off component as described above in the second aspect to the rim 14 of the opening. In that way, the fluid on/off body 4 serves as a part of the first channel wall 11, the on/off member 5 can extend from the first fluid channel 1 of the fluid on/off apparatus into a second fluid channel 2 in the fluid on/off apparatus; thus, when the first fluid is not supplied through the first fluid channel 1, the on/off member 5 can block the second fluid channel 2 to stop the supply of the second fluid; when the first fluid is supplied through the first fluid channel 1, the first fluid applies pressure on the sliding plate 7, the flexible connecting member is deformed flexibly, the pressure applied by the first fluid on the sliding plate 7 drives the sliding plate 7 to move, thereby drive the on/off member 5 to move so as to unblock the second fluid channel, thereby the second fluid can be supplied through the second fluid channel. In that way, the supply of the second fluid can be controlled by controlling the supply of the first fluid, thereby the safety and reliability of the supply of the second fluid can be improved. For example, when the fluid on/off housing is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

In addition, in the fluid channel housing, other fluid channels may be provided between the first fluid channel 1 and the second fluid channel 2, and the on/off member 5 may extend into the second fluid channel 2 through the other fluid channels. Alternatively, as shown in FIGS. 1 and 2, a shared channel wall 16 between the first fluid channel 1 and the second fluid channel 2 includes a through-channel configured to mount the on/off member 5 of the fluid on/off component described above in the second aspect. Thus, the internal structure of the fluid channel housing can be simplified accordingly, and the reliability of the movement of the on/off member 5 can be improved.

In a fourth aspect, the present disclosure provides a fluid on/off apparatus. In different embodiments shown in FIGS. 1-12, the fluid on/off apparatus comprises a fluid on/off housing 3 and a fluid on/off component, wherein a first fluid channel 1 and a second fluid channel 2 that are isolated from each other are provided in the fluid on/off housing 3, the fluid on/off component comprises a fluid on/off body 4 and an on/off member 5, wherein the fluid on/off body 4 is movably arranged in the first fluid channel 1, the on/off member 5 is connected to the fluid on/off body 4, extends from the first fluid channel 1 into the second fluid channel 2, and is movable; wherein the on/off member 5 blocks the second fluid channel 2 when the pressure applied by a first fluid in the first fluid channel 1 on the fluid on/off body 4 is smaller than a pressure required for the fluid on/off body to move; and wherein the fluid on/off body 4 moves and drives the on/off member 5 to move to unblock the second fluid channel 2 when the pressure applied by the first fluid in the first fluid channel 1 on the fluid on/off body 4 is greater than the pressure required for the fluid on/off body 4 to move.

In the technical scheme, the fluid on/off body 4 is movably arranged in the first fluid channel 1, the on/off member 5 is connected to the fluid on/off body 4, extends from the first fluid channel 1 into the second fluid channel 2 and is movable; thus, when the pressure in the first fluid channel 1 applied on the fluid on/off body 4 is smaller than a pressure required for the fluid on/off body 4 to move, for example, when the supply of the first fluid in the first fluid channel 1 is stopped, the on/off member 5 blocks the second fluid channel 2, so as to stop the supply of the second fluid through the second fluid channel 2; when the first fluid is supplied through the first fluid channel 1 and the pressure applied by the first fluid in the first fluid channel on the fluid on/off body is greater than the pressure required for the fluid on/off body to move, the fluid on/off body 4 can move and drive the on/off member 5 to move, so as to unblock the second fluid channel 2 to supply the second fluid. In that way, the supply of the second fluid can be controlled by controlling the supply of the first fluid, thereby the safety and reliability of the supply of the second fluid can be improved. For example, when the fluid on/off apparatus is applied in a ventilation treatment device, the first fluid may be air flow supplied by a fan, the second fluid may be oxygen supplied from an oxygen source; thus, oxygen waste can be avoided, and the safety of use of oxygen in the ventilation treatment device can be improved significantly.

In addition, in the fluid on/off apparatus, in an embodiment, as described above, the fluid on/off body 4 may be arranged in the first fluid channel 1. Alternatively, in another embodiment, as shown in FIG. 1, the fluid on/off body 4 serves as a part of the first channel wall 11 of the first fluid channel 1, which may be implemented in a variety of ways. For example, a cylinder is formed on the first channel wall 11, the fluid on/off body 4 is arranged in the cylinder in a slidingly sealed manner; thus, since the fluid on/off body 4 is encapsulated in the cylinder, it serves as a part of the first channel wall 11.

Figure 3:
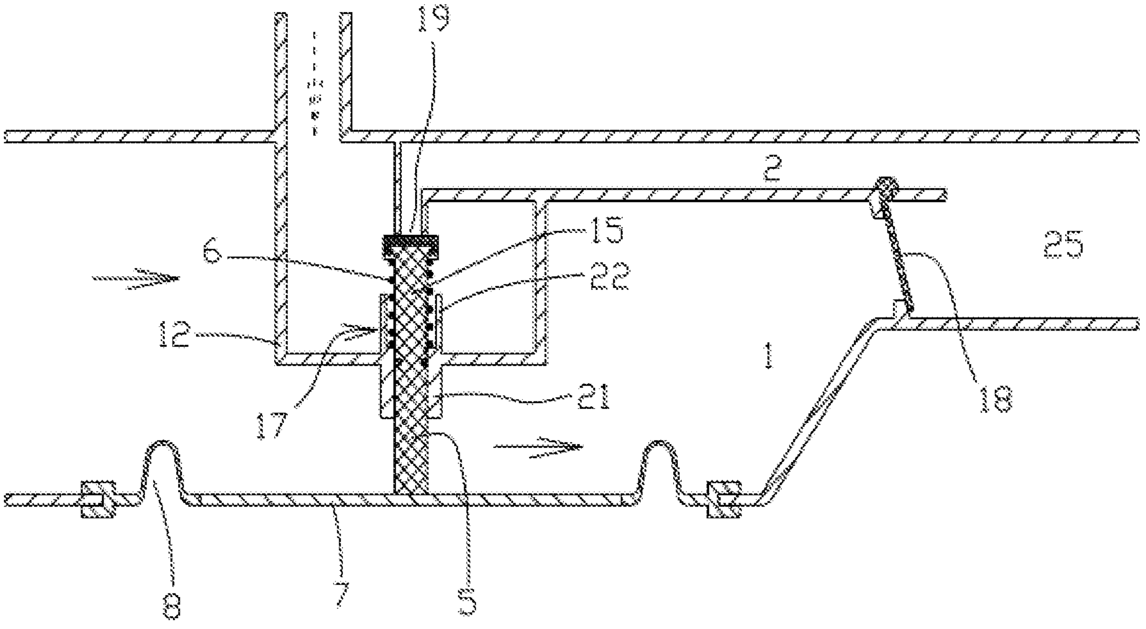
FIG. 3 is a schematic structural diagram of a fluid on/off apparatus provided in second embodiment of the present disclosure, in which the on/off member blocks the second fluid channel.
Figure 4:
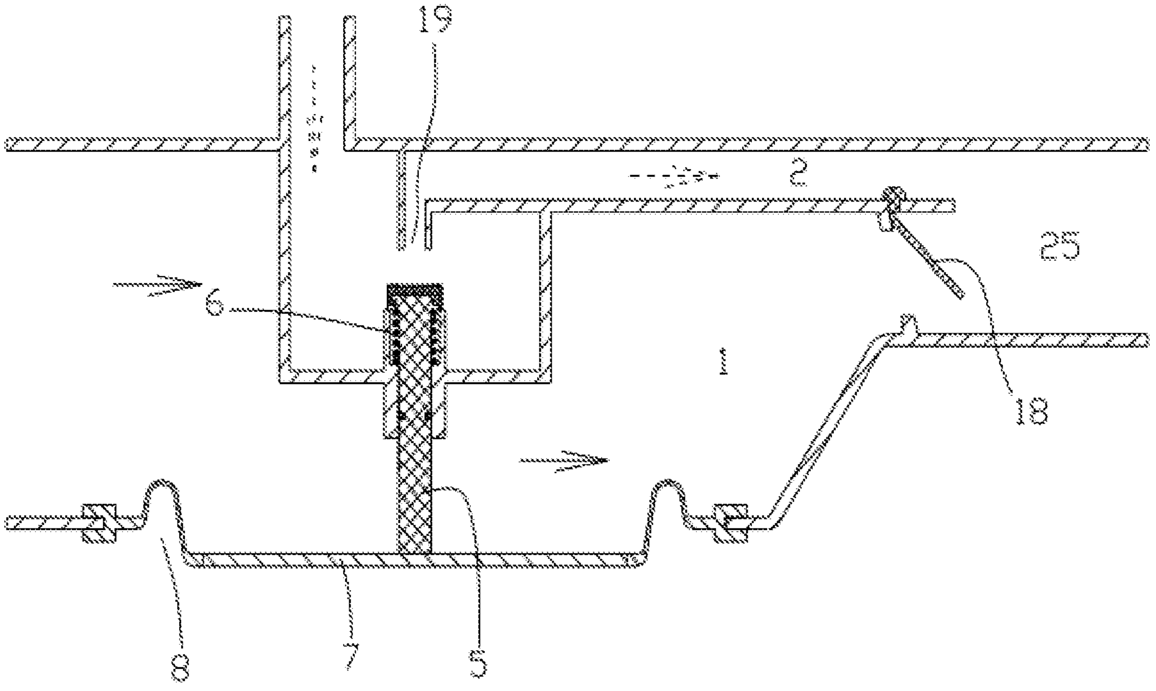
FIG. 4 is a schematic diagram of the fluid on/off apparatus in FIG. 3, in which the on/off member unblocks the second fluid channel.

Furthermore, as shown in FIG. 3, the fluid on/off apparatus comprises an elastic member 6, which can apply an elastic pre-pressure on the on/off member 5 so that the on/off member 5 blocks the second fluid channel 2, when the pressure in the first fluid channel 1 applied on the fluid on/off body 4 is smaller than the pressure required for the fluid on/off body 4 to move. Thus, by means of the elastic pre-pressure applied by the elastic member 6 on the on/off member 5, the on/off member 5 can block the second fluid channel 2 more stably and more reliably.

Figure 5:
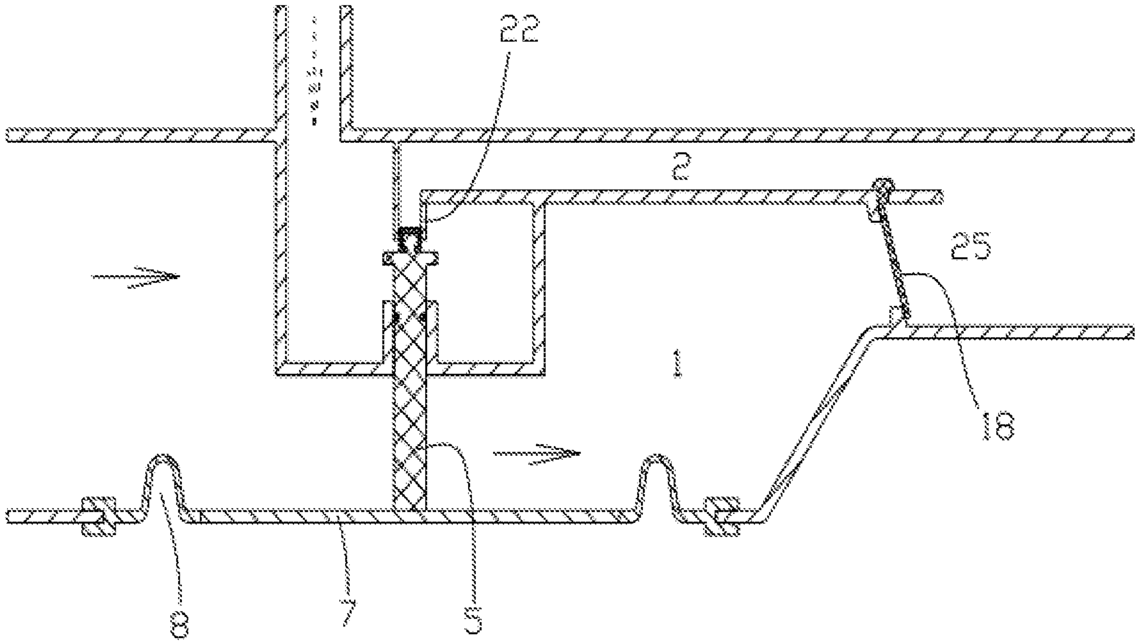
FIG. 5 is a schematic structural diagram of a fluid on/off apparatus provided in third embodiment of the present disclosure, in which the on/off member blocks the second fluid channel.
Figure 6:
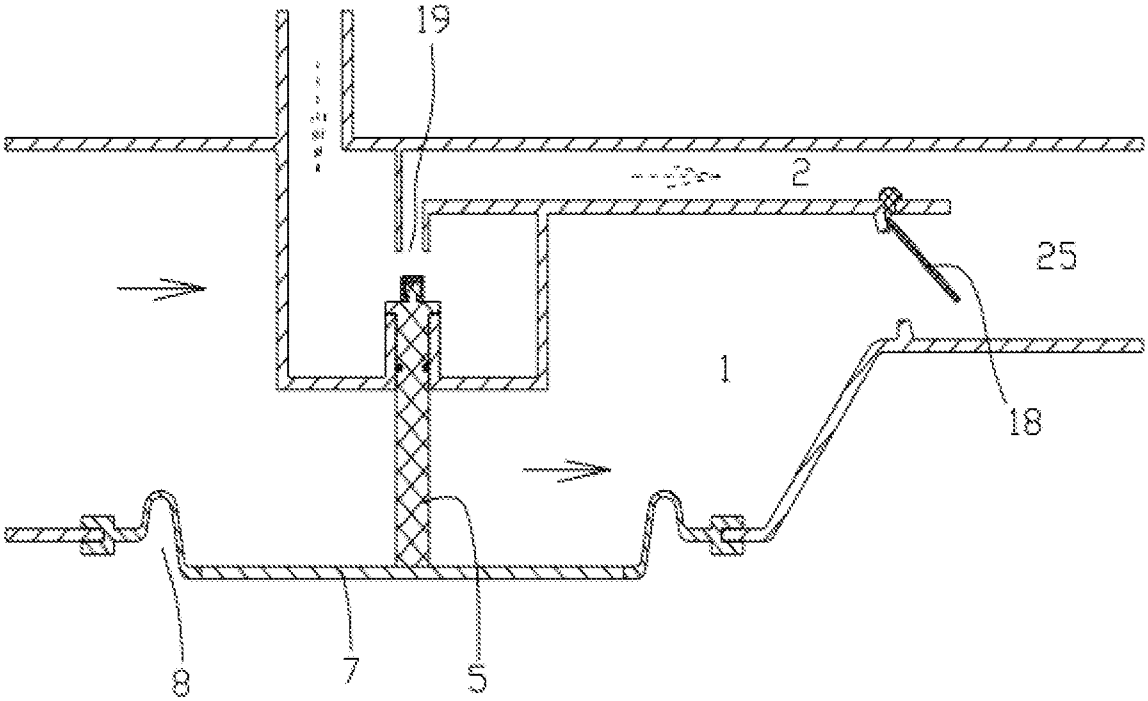
FIG. 6 is a schematic diagram of the fluid on/off apparatus in FIG. 5, in which the on/off member unblocks the second fluid channel.
Figure 9:
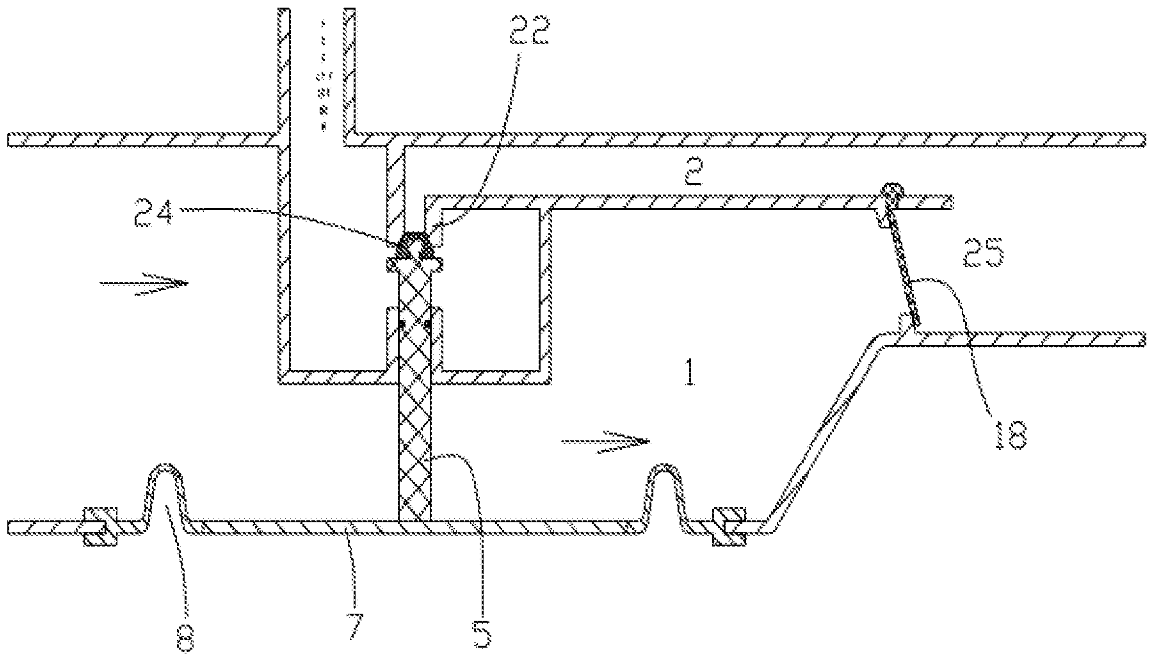
FIG. 9 is a schematic structural diagram of a fluid on/off apparatus provided in fifth embodiment of the present disclosure, in which the on/off member blocks the second fluid channel.

Of course, the elastic member 6 may be in a variety of structures and forms of arrangement. For example, as shown in FIGS. 1, 5 and 9, the fluid on/off body 4 comprises an elastic member 6. For example, the elastic member 6 may be connected between the sliding plate 7 and the channel wall of the first fluid channel 1, as long as it can apply an elastic pre-pressure on the on/off member 5. The elastic member 6 may be a spring or elastic strip.

In addition, in the fluid on/off apparatus, the fluid on/off component may be in variety of structural forms. However, the fluid on/off component may be in a structural form, as long as it can achieve the above-mentioned effect. For example, the fluid on/off component may comprise a base plate, an on/off member 5, and a spring connected between the base plate and the channel wall of the first fluid channel 1. Alternatively, the fluid on/off component is the fluid on/off component described above in the second aspect, wherein the flexible connecting member is connected to the first channel wall 11 of the first fluid channel 1. Thus, the sliding plate 7 can drive the on/off member 5 to move, by means of the flexible deformation of the flexible connecting member.

In addition, as described above, in the case that the flexible connecting member is an elastic skirt 8, the elastic skirt 8 can play the role of the elastic member 6; here, the elastic skirt 8 may be regarded as the elastic member. Thus, the elastic skirt 8 can return to its original position under the action its elastic force; in addition, after the elastic skirt 8 returns to its original position, the elastic skirt 8 may be used to apply a pre-pressure on the on/off member 5 connected to the sliding plate 7, so that the on/off member 5 keeps the second fluid channel 2 in a blocked state under the pre-pressure. Here, when the first fluid is supplied, the pressure of the first fluid applied on the sliding plate 7 has to overcome the pre-pressure applied by the elastic skirt 8 before the elastic skirt 8 can be deformed elastically to allow the sliding plate 7 to move, so as to drive the on/off member 5 to move to unblock the second fluid channel 2.

In addition, in the fluid on/off apparatus, the fluid on/off housing 3 may be in a variety of structural forms. In an embodiment, the fluid on/off housing 3 is the fluid channel housing 3 described above in the third aspect, wherein the flexible connecting member is connected to the rim 14 of the opening, so that the fluid on/off body 4 serves as a part of the first channel wall 11.

Furthermore, as shown in FIGS. 1 and 2, the flexible connecting member comprises a U-shaped wall 9 extending into the first fluid channel 1, and an opening of the U-shaped wall 9 is oriented to the outside of the first fluid channel 1. Thus, the U-shaped wall 9 can utilize the bent side walls to effectively increase the stroke of the sliding plate 7. For example, in the case that the flexible connecting member is an elastic skirt 8, the sliding plate 7 drives the bottom wall and the two side walls of the U-shaped wall 9 to deform when the sliding plate 7 moves outward under the pressure of the first fluid, thereby the U-shaped wall 9 can store higher elastic restoring energy, so that the sliding plate 7 can be returned to its original position more easily, and a higher pre-pressure can be applied to the on/off member 5 connected to the sliding plate 7, so that the on/off member 5 can block the second fluid channel 2 more stably and more reliably.

Figure 7:
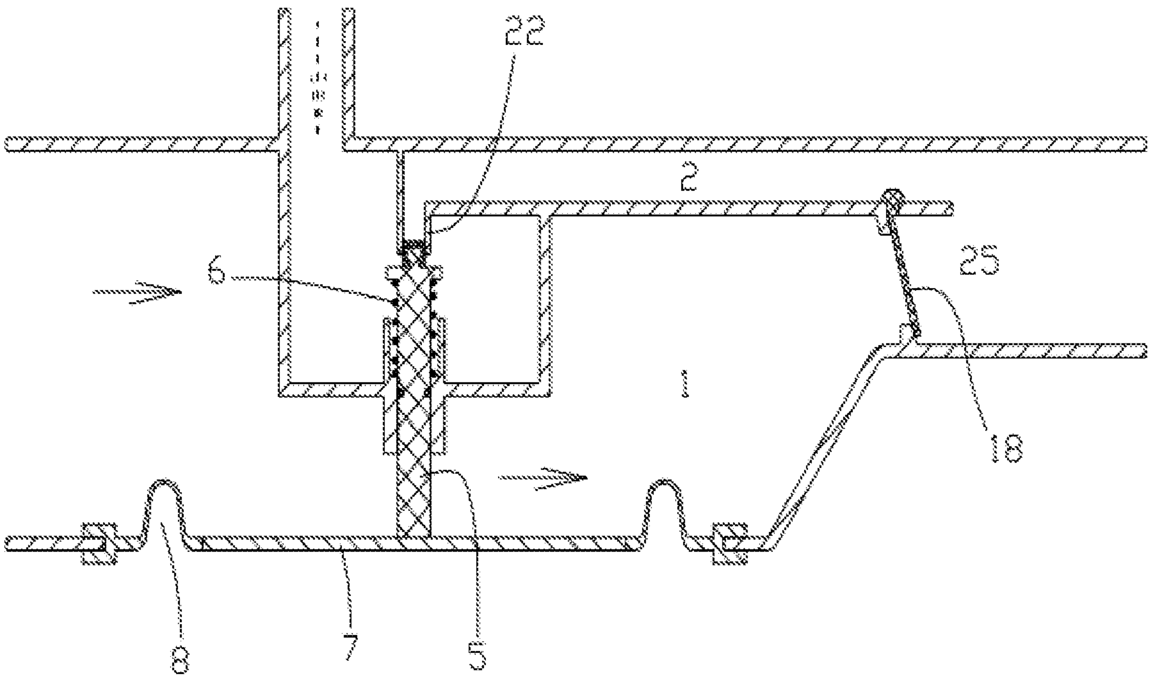
FIG. 7 is a schematic structural diagram of a fluid on/off apparatus provided in fourth embodiment of the present disclosure, in which the on/off member blocks the second fluid channel.
Figure 8:
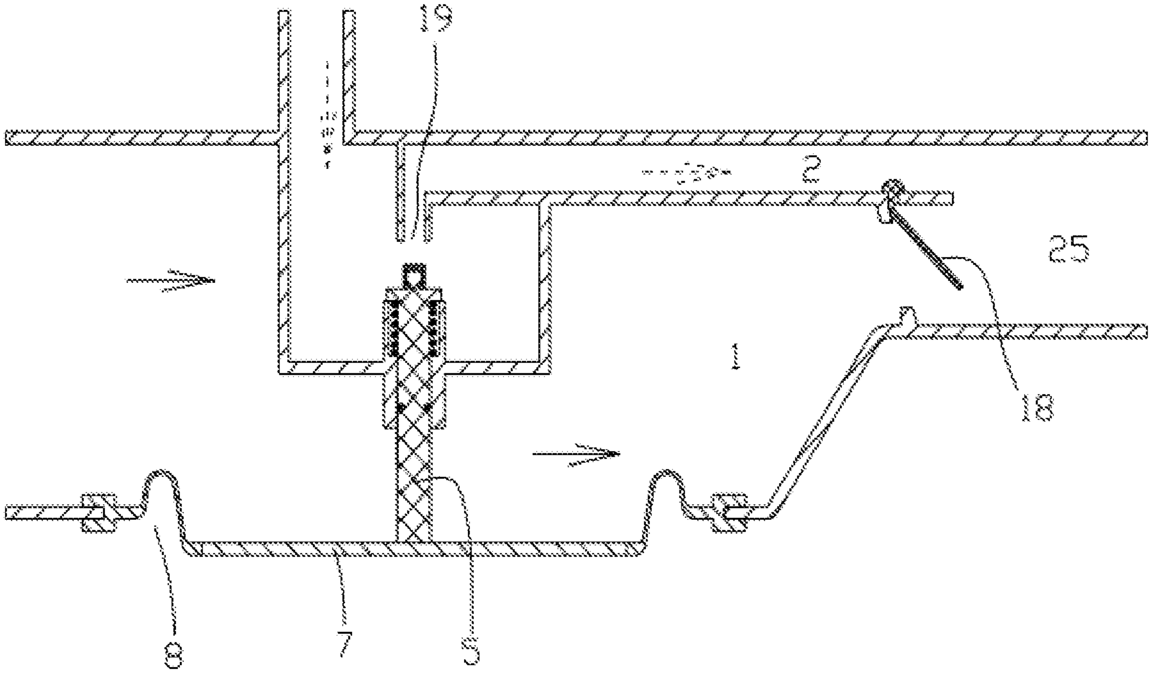
FIG. 8 is a schematic diagram of the fluid on/off apparatus in FIG. 7, in which the on/off member unblocks the second fluid channel.
Figure 11:
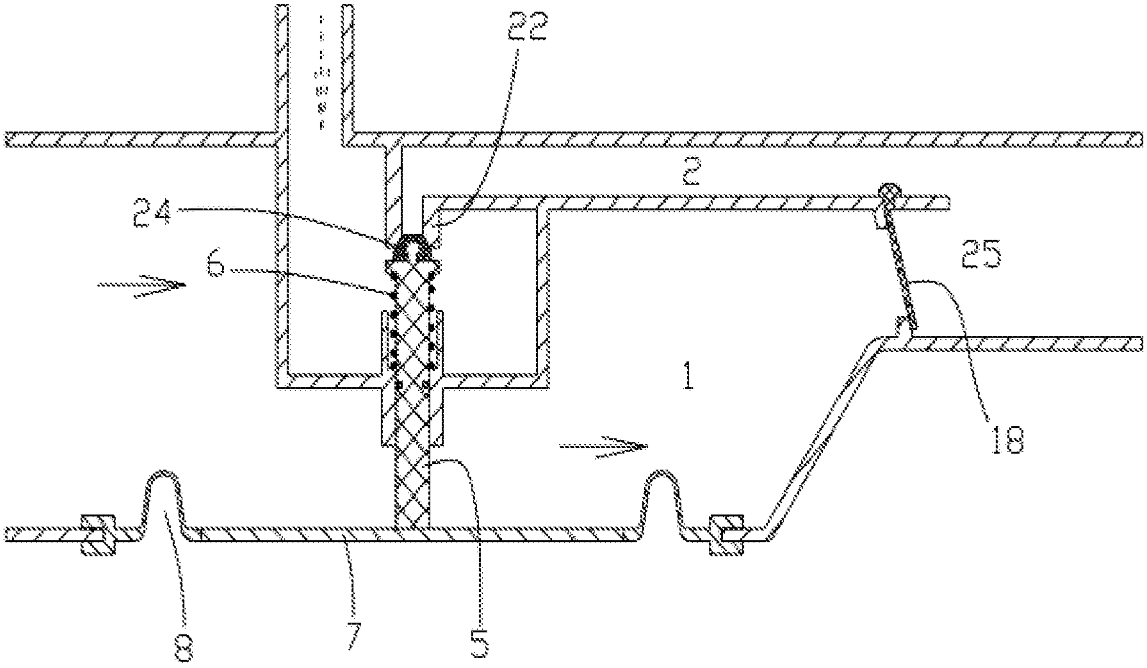
FIG. 11 is a schematic structural diagram of a fluid on/off apparatus provided in sixth embodiment of the present disclosure, in which the on/off member blocks the second fluid channel.
Figure 12:
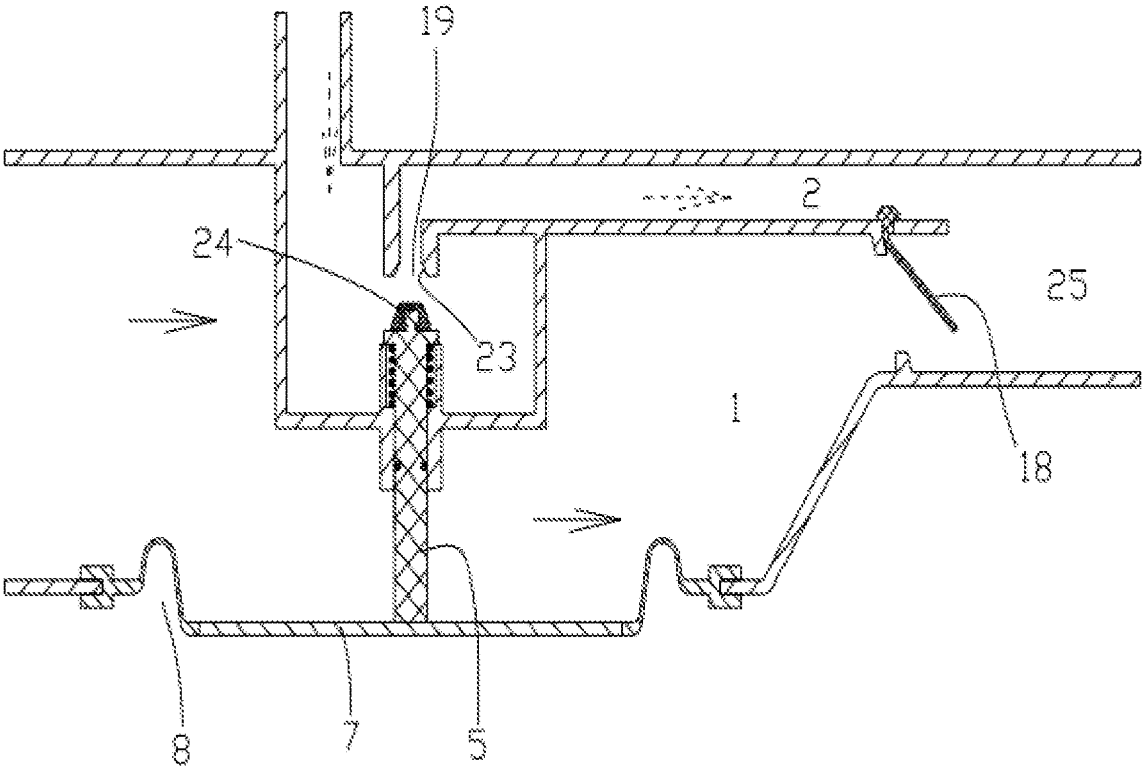
FIG. 12 is a schematic diagram of the fluid on/off apparatus in FIG. 11, in which the on/off member unblocks the second fluid channel.

In addition, as shown in FIGS. 3, 7 and 11, the elastic member 6 may be arranged between the second channel wall 12 of the second fluid channel 2 and an on/off section 15 of the on/off member 5 extending into the second fluid channel 2; thus, in a structure in which the fluid on/off body 4 includes the flexible connecting member, the flexible connecting member may have no elasticity or have essentially negligible elasticity, so that the flexible connecting member of the fluid on/off body 4 can be formed conveniently; for example, the flexible connecting member may employ a bellow pipe section. Of course, alternatively the flexible connecting member may have elasticity.

In addition, as shown in FIG. 1, a shared channel wall 16 between the first fluid channel 1 and the second fluid channel 2 comprises a guiding mounting cylinder 17 having a through-channel, and the on/off member 5 is inserted in the guiding mounting cylinder 17 in an axially movable manner. Thus, by means of the guiding mounting cylinder 17, the movement guiding stroke of the on/off member 5 can be increased, thereby the movement of the on/off member 5 is smoother and more stable.

In addition, as shown in FIG. 3, the guiding mounting cylinder 17 may comprise a second cylinder section 22 extending into the second fluid channel 2 and a first cylinder section 21 extending into the first fluid channel 1; thus, the movement guiding stroke of the on/off member 5 can be further increased, and the movement of the on/off member 5 is smoother and more stable.

Furthermore, as shown in FIG. 3, in an embodiment, the fluid on/off apparatus comprises an elastic member 6 that is sleeved on the on/off member 5 and abuts between the elastic member 6 and a stop flange in the guiding mounting cylinder 17, and the stop flange may be located in the first cylinder section 21 or in the second cylinder section 22; when the pressure in the first fluid channel 1 applied on the fluid on/off body 4 is smaller than a pressure required for the fluid on/off body to move, the elastic member 6 can apply an elastic pre-pressure on the on/off member 5, so that the on/off member 5 blocks the second fluid channel 2. Thus, the elastic member 6 can be positioned stably and reliably by means of the second cylinder section 22, so that any sway of the elastic member 6 in the elastic deformation process can be avoided.

Furthermore, as shown in FIGS. 1 and 2, in the fluid flow direction as indicated by the dotted line and solid arrow in FIGS. 1 and 2, the first fluid channel 1 is provided with a first fluid discharging check valve 18 downstream from the on/off member 5 and the fluid on/off body 4, and the first fluid discharging check valve 18 can prevent the second fluid in the second fluid channel 2 from entering the first fluid channel 1 when the pressure of the second fluid in the second fluid channel 2 is greater than the pressure of the first fluid in the first fluid channel 1. In an embodiment, the first fluid discharging check valve 18 may be opened after the on/off member 5 unblocks the second fluid channel 2, for example, the start pressure of the first fluid discharging check valve 18 is greater than a pressure required for move; thus, when the first fluid applies pressure on the fluid on/off body 4, the first fluid discharging check valve 18 remains in a closed state, till the on/off member 5 unblocks the second fluid channel 2; then the first fluid discharging check valve 18 is opened to allow the first fluid to pass as the pressure of the first fluid is increased. In another embodiment, the first fluid discharging check valve 18 may be opened while the second fluid channel 2 is unblocked. In yet another embodiment, the first fluid discharging check valve 18 may be opened before the second fluid channel is unblocked; for example, as the pressure of the first fluid is increased, e.g., as the rotation speed of the fan is increased, the first fluid discharging check valve 18 is opened first; then, when the pressure reaches a certain value, the pressure can drive the on/off member 5 to unblock the second fluid channel.

Furthermore, in different embodiments shown in FIGS. 1-12, the second fluid channel 2 is provided with a blocking cylinder 20 having a fluid inlet 19, an internal flow channel of the blocking cylinder 20 serves as a part of the fluid channel 2, the on/off member 5 can be pressed on an open end face of the blocking cylinder 20 to block the fluid inlet 19, and/or the on/off member 5 can enter the blocking cylinder 20 to block the fluid inlet 19, so as to block the second fluid channel 2. Thus, by utilizing the blocking cylinder 20, a smaller flow area can be used to realize the blocking/unblocking of the second fluid channel, thereby the structure is compact.

Figure 10:
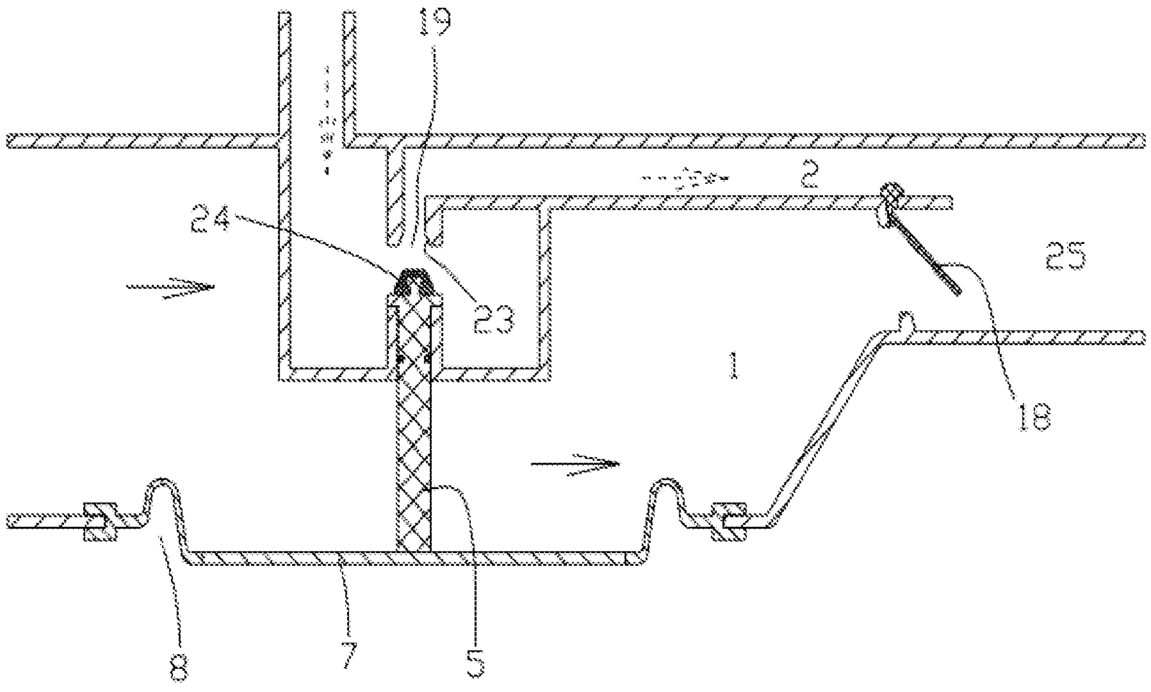
FIG. 10 is a schematic diagram of the fluid on/off apparatus in FIG. 9, in which the on/off member unblocks the second fluid channel.

Furthermore, as shown in FIGS. 9 and 10, the fluid inlet 19 comprises a tapered section 23 with a gradually reduced inner diameter, and the on/off member 5 comprises a tapered end plug 24 with a gradually reduced outer diameter, which is to be fitted with the tapered section 23 with a gradually reduced inner diameter. Thus, the tapered end plug 24 with a gradually reduced outer diameter can enter the tapered section with a gradually reduced inner diameter and contact with the tapered section 23 in a sealed manner by shape fitting, thereby the blocking of the second fluid channel 2 is more stable and more reliable.

Furthermore, as shown in FIGS. 1 and 2, a fluid mixing channel 25 is provided in the fluid on/off housing 3, and an outlet end of the first fluid channel 1 and an outlet end of the second fluid channel 2 are in communication with the fluid mixing channel 25. Thus, the first fluid and the second fluid can be mixed in the fluid mixing channel 25, and the mixed fluid can flow out of the fluid mixing channel 25 via the outlet.

In addition, the fluid on/off apparatus may be used for blocking/unblocking control for the supply of any fluid. For example, in an embodiment, as shown in FIG. 1, the first fluid channel 1 serves as an air delivery channel, and an inlet end of the first fluid channel 1 serves as a fan connecting end 26, the second fluid channel 2 serves as an oxygen delivery channel. Thus, as described above, the supply of oxygen can be controlled stably and reliably, thereby oxygen waste can be avoided, and the safety of use of oxygen in a ventilation treatment device can be improved significantly.

In a fifth aspect, the present disclosure provides an oxygen supply control method for controlling the oxygen supply of a ventilation treatment device, which comprises: arranging an oxygen valve in an oxygen supply channel and an air supply channel that is in communication with a fan; controlling the air flow provided by a fan to apply pressure on an oxygen valve so that the oxygen valve opens the oxygen supply channel to supply oxygen, when the ventilation treatment device is powered on and the fan operates; and controlling the oxygen valve to block the oxygen supply channel under the elastic restoring force of the elastic member to stop the oxygen supply when the ventilation treatment device is powered off or the fan is abnormal or the fan stops owing to circuit abnormalities during the operation of the ventilation treatment device.

Thus, the supply of oxygen cay be controlled stably and reliably by means of an oxygen valve arranged movably in an oxygen supply channel and an air supply channel in communication with the fan and by utilizing the pressure applied by the air flow supplied by the fan, thereby oxygen waste can be avoided, and the safety of use of oxygen in the ventilation treatment device can be improved significantly.

In the oxygen supply control method, the oxygen valve may be a swing valve, and comprises an oxygen blade extending into the oxygen supply channel and an air blade extending into the air supply channel. The air flow provided by the fan can push the air blade to swing, thereby drives the oxygen blade to swing, so that the oxygen supply channel is unblocked to supply oxygen. Alternatively, the oxygen supply control method may be implemented by the fluid on/off apparatus described above.

Figure 13:
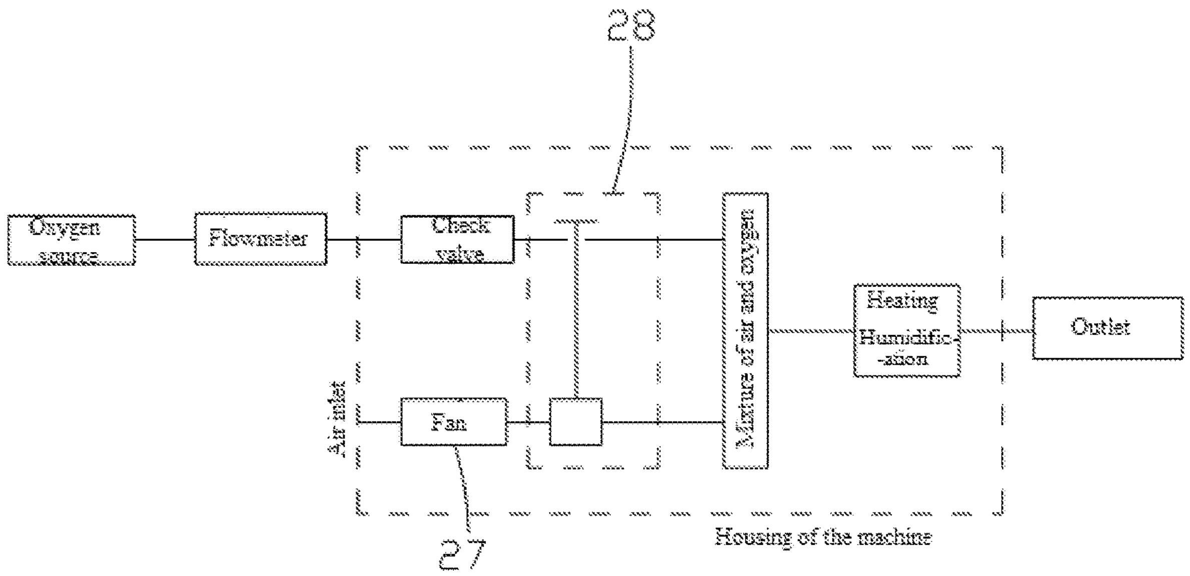
FIG. 13 is a schematic diagram of a ventilation treatment device provided in an embodiment of the present disclosure during use.

In a sixth aspect, the present disclosure provides a ventilation treatment device. As shown in the schematic diagram of the use of the ventilation treatment device in FIG. 13, the ventilation treatment device comprises a fan 27 and the fluid on/off apparatus 28 as described above in the fourth aspect, wherein the first fluid channel 1 serves as an air delivery channel, an inlet end of the first fluid channel 1 is in communication with an outlet end of the fan 27, and the second fluid channel 2 serves as an oxygen delivery channel. Thus, as described above, the safety of use of oxygen in the ventilation treatment device is improved significantly, and the overall performance of the ventilation treatment device is improved.

Alternatively, the ventilation treatment device can implement the oxygen supply control method as described above in the fifth aspect. Thus, as described above, the safety of use of oxygen in the ventilation treatment device is improved significantly, and the overall performance of the ventilation treatment device is improved.

The ventilation therapy device may be a ventilator or a high-flow oxygen therapy device.

While some preferred embodiments of the present disclosure are described above with reference to the accompanying drawings, the present disclosure is not limited to the details in those embodiments. Those skilled in the art can make various simple modifications and variations to the technical scheme of the present disclosure, without departing from the technical concept of the present disclosure. However, all these simple modifications and variations shall be deemed as falling in the scope of protection of the present disclosure.

In addition, it should be noted that the specific technical features described in the above embodiments may be combined in any appropriate form, provided that there is no conflict among them. To avoid unnecessary repetition, various possible combinations are not described specifically in the present disclosure.

Moreover, different embodiments of the present disclosure may also be combined freely as required, as long as the combinations don't deviate from the ideal of the present disclosure. However, such combinations shall also be deemed as being disclosed in the present disclosure.

The invention claimed is:

1. A fluid on/off apparatus, comprising:

a fluid on/off housing, in which a first fluid channel and a second fluid channel that are isolated from each other are provided; and a fluid on/off component, comprising a fluid on/off body and an on/off member, wherein the fluid on/off body is movably arranged in the first fluid channel, the on/off member is connected to the fluid on/off body and the on/off member extends into the second fluid channel from the first fluid channel and is movable, and the fluid on/off body comprises a sliding plate and a flexible connecting member, wherein the flexible connecting member is connected to the sliding plate, and is configured to connect to a first channel wall of the first fluid channel, and the sliding plate is configured to move, driven by a pressure of a first fluid in the first fluid channel, to drive the flexible connecting member to deform flexibly and to drive the on/off member to move to unblock the second fluid channel, wherein the flexible connecting member is an elastic skirt, which applies an elastic pre-pressure on the on/off member so that the on/off member blocks the second fluid channel when a pressure applied by the first fluid in the first fluid channel on the fluid on/off body is smaller than a pressure required for the fluid on/off body to move, and wherein the fluid on/off body moves and drives the on/off member to move to unblock the second fluid channel when the pressure applied by the first fluid in the first fluid channel on the fluid on/off body is greater than the pressure required for the fluid on/off body to move.

2. The fluid on/off apparatus of claim 1, wherein the fluid on/off body serves as a part of the first channel wall of the first fluid channel.

3. The fluid on/off apparatus of claim 1, wherein the fluid on/off apparatus comprises an elastic member, which applies the elastic pre-pressure on the on/off member so that the on/off member blocks the second fluid channel, when the pressure in the first fluid channel applied on the fluid on/off body is smaller than the pressure required for the fluid on/off body to move.

4. The fluid on/off apparatus of claim 1, wherein the flexible connecting member is an annular flexible connecting member and connected to a periphery of the sliding plate.

5. The fluid on/off apparatus of claim 1, wherein the first channel wall of the first fluid channel has an opening configured to connect the flexible connecting member, so that the fluid on/off body of the fluid on/off component serves as a part of the first channel wall of the first fluid channel.

6. The fluid on/off apparatus of claim 5, wherein the flexible connecting member comprises a U-shaped wall extending into the first fluid channel, and an opening of the U-shaped wall is oriented to an outside of the first fluid channel.

7. The fluid on/off apparatus of claim 3, wherein the elastic member is arranged between a second channel wall of the second fluid channel and an on/off section of the on/off member which extends into the second fluid channel.

8. The fluid on/off apparatus of claim 1, wherein a shared channel wall between the first fluid channel and the second fluid channel comprises a guiding mounting cylinder having a through-channel, and the on/off member is inserted in the guiding mounting cylinder in an axially movable manner.

9. The fluid on/off apparatus of claim 8, wherein the guiding mounting cylinder comprises a first cylinder section extending into the first fluid channel and a second cylinder section extending into the second fluid channel.

10. The fluid on/off apparatus of claim 9, wherein the fluid on/off apparatus comprises an elastic member that is sleeved on the on/off member, wherein the elastic member applies an elastic pre-pressure on the on/off member so that the on/off member blocks the second fluid channel when the pressure in the first fluid channel applied on the fluid on/off body is smaller than the pressure required for the fluid on/off body to move.

11. The fluid on/off apparatus of claim 1, wherein the first fluid channel is provided with a first fluid discharging check valve downstream from the on/off member and the fluid on/off body in a fluid flow direction.

12. The fluid on/off apparatus of claim 1, wherein the second fluid channel is provided with a blocking cylinder having a fluid inlet, an internal flow channel in the blocking cylinder serves as a part of fluid channel sections of the second fluid channel, the on/off member can be pressed on an open end face of the blocking cylinder to block the fluid inlet, and/or the on/off member can enter the blocking cylinder to block the fluid inlet, so as to block the second fluid channel.

13. The fluid on/off apparatus of claim 12, wherein the fluid inlet comprises a tapered section with a gradually reduced inner diameter, and the on/off member comprises a tapered end plug with a gradually reduced outer diameter, which is to be fitted with the tapered section with a gradually reduced inner diameter.

14. The fluid on/off apparatus of claim 1, wherein a fluid mixing channel is provided in the fluid on/off housing, and an outlet end of the first fluid channel and an outlet end of the second fluid channel are in communication with the fluid mixing channel.

15. The fluid on/off apparatus of claim 1, wherein the first fluid channel serves as an air delivery channel, an inlet end of the first fluid channel serves as a fan connecting end, and the second fluid channel serves as an oxygen delivery channel.

16. A ventilation treatment device, comprising a fan and the fluid on/off apparatus of claim 1, wherein the first fluid channel serves as an air delivery channel, an inlet end of the first fluid channel is in communication with an outlet end of the fan, and the second fluid channel serves as an oxygen delivery channel.

* * * * *